United States Patent
Finkelshteins

(10) Patent No.: US 6,635,016 B2
(45) Date of Patent: Oct. 21, 2003

(54) METHOD AND SYSTEM FOR COLLECTING AND PROCESSING OF BIOMEDICAL INFORMATION

(75) Inventor: Jehezkelis Finkelshteins, Riga (LV)

(73) Assignee: Joseph Finkelstein, Brookline, MA (US)

(*) Notice: Subject to any disclaimer, the term of this patent is extended or adjusted under 35 U.S.C. 154(b) by 0 days.

(21) Appl. No.: 09/933,636

(22) Filed: Aug. 20, 2001

(65) Prior Publication Data

US 2002/0022775 A1 Feb. 21, 2002

(30) Foreign Application Priority Data

Aug. 21, 2000 (LV) .................................. 12612

(51) Int. Cl.[7] ................................................ A61B 5/00
(52) U.S. Cl. ...................... 600/300; 128/903; 128/904
(58) Field of Search ................................. 600/300, 301; 128/897, 898, 903, 904, 920; 702/19; 73/1.34; 607/27, 32, 60

(56) References Cited

U.S. PATENT DOCUMENTS

| | | | |
|---|---|---|---|
| 4,296,756 A | 10/1981 | Dunning et al. ............. 128/716 |
| 5,241,469 A | 8/1993 | Nelson et al. ........... 364/413.03 |
| 5,347,843 A | * 9/1994 | Orr et al. ........................ 73/1.34 |
| 5,549,117 A | 8/1996 | Tacklind et al. .............. 128/716 |
| 5,626,144 A | 5/1997 | Tacklind et al. .............. 128/725 |
| 5,704,366 A | 1/1998 | Tacklind et al. .............. 128/716 |
| 5,732,709 A | 3/1998 | Tacklind et al. .............. 128/726 |
| 5,827,179 A | 10/1998 | Lichter et al. ................ 600/300 |
| 5,860,917 A | * 1/1999 | Comanor et al. ............ 600/300 |
| 6,264,614 B1 | * 7/2001 | Albert et al. ................. 128/904 |
| 6,289,115 B1 | * 9/2001 | Takeo ............................ 128/920 |

OTHER PUBLICATIONS

Joseph Finkelstein, et al. "Potential Role of Telecommunication Technologies in the Management of Chronic Health Conditions", Dis Manage Health Outcomes Aug. 8, 2000 (2) 57–63.
Vitalograph®, "2120 Hand Held Storage Spirometer User Manual", 1997, pp. i–66.
Vitalograph®, "Spirotrac III User Manual", 1997, pp. i–139.

* cited by examiner

Primary Examiner—Eric F. Winakur
Assistant Examiner—David J. McCrosky
(74) Attorney, Agent, or Firm—David D. Lowry; Brown Rudnick Berlack Israels LLP

(57) ABSTRACT

A system and method for collecting biomedical information from a patient. A data measurement component including at least one sensing component is provided, the sensing component providing signals representing sensed patient data to a communications port, the communications port to allow connection to a computer system through a computer system communications port. A remote server includes one or more specialized software modules, which are capable of communicating with the data measurement component through the computer system communications port. The remote server, upon receiving a request from the computer system, will transmit one of the specialized software modules which is appropriate for collecting and interpreting the signals representing sensed patient data from the at least one sensing component. The specialized software module sent by the remote server, after it is received by the computer system, initializes and controls the operation of the data measurement components.

24 Claims, 13 Drawing Sheets

S – SENSOR
C – COMPUTER CARD CONTAINING ADC, ADDRESS DECODER AND AN ELECTRONIC CIRCUIT PROVIDING SIGNAL COMPLIANCE WITH THE INTERFACE

S- SENSOR

C- COMPUTER CARD CONTAINING ADC, ADDRESS DECODER AND AN ELECTRONIC CIRCUIT PROVIDING SIGNAL COMPLIANCE WITH THE INTERFACE

S – SENSOR

C – COMPUTER CARD CONTAINING ADC, ADDRESS DECODER AND AN ELECTRONIC CIRCUIT PROVIDING SIGNAL COMPLIANCE WITH THE INTERFACE

METHOD AND SYSTEM FOR COLLECTING AND PROCESSING OF BIOMEDICAL INFORMATION

FIELD OF THE INVENTION

This invention is directed towards electronic data collection, and more particularly towards a system and method for remote collection and processing of biomedical data.

BACKGROUND

As medical science advances, more and better sensors and equipment are available to help monitor and maintain patients. However, such equipment is often expensive and difficult to properly use. Therefore, many patients must visit medical facilities on a regular basis in order to have tests and measurements done. This is expensive and inconvenient for many patients on an out-patient basis. Providing biomedical sensors and equipment which can be used by patients and users in their homes is a reasonable and cost saving solution. But biomedical systems in medical offices and especially in patients homes may frequently be used by users with minimal technical skills and therefore the exploitation of such systems should be as simple as possible. To make such systems affordable for a widespread use at patient homes the system's cost should be minimized, including cost of hardware and software.

A real-time system for collection and processing of biomedical data using cards inserted in the slots of PC that supports the PCMCIA bus standard was previously described in U.S. Pat. No. 5,827,179 and issued to Lichter. The PCMCIA bus was designed for portable PC types such as "laptop" and "notebook." In accordance with Lichter, each additional biomedical signal requires an additional PCMCIA card. Thus the number of cards needed is equal to the number of signals to be measured. This makes the system described in Lichter cumbersome and expensive. Additional disadvantage of such an approach is related to the fact that not all manufacturers produce PCMCIA-compatible PCs. To overcome the incompatibility problem four PCMCIA standards were designed—from PCMCIA type 1 to PCMCIA type 4.

The approach proposed in Lichter also requires that the software that controls the process of collecting and processing the incoming biomedical information from each PCMCIA card, be permanently installed in the user's PC. As a result the user have to purchase the specialized data acquisition software which increases the cost of the system. In addition, the user must possess sufficient technical skills to install the specialized software. This complicates the usage of the system not only at the stage of initial installation of the specialized software but also each time when software upgrade installation is required.

A remote pulmonary function tester to assess lung function at a patient's home and to transmit the collected information to a remote data center was previously described in U.S. Pat. No. 4,296,756 and issued to Dunning. According to Dunning, the information was sent via a telephone line to a central computer to assess patient functional status. The tester consisted from pressure transducer, Analog-to-Digital Converter (ADC), keyboard for alphanumeric data entry, microprocessor system for data storage and identification, modem interface to communicate with the central computer over telephone line and a microprocessor to control the tester. The functionality of the system is permanently limited by analysis of a predefined set of lung function parameters without a possibility of any modification. The signal acquisition and data analysis software must be permanently installed in the user's computer.

A system for monitoring and reporting medical measurements and transmission of the collected information to remote terminal for assessment by a clinician was described in such patents as U.S. Pat. Nos. 5,549,117; 5,626,144; 5,704,366; and 5,732,709, all to Tacklind et al. The system is similar to the one described in Lichter since software for data collections, analysis and transfer should reside permanently in the user's microprocessor unit. The system is for analysis of one signal exclusively.

A method and apparatus for automated spirometry data acquisition and processing was described in U.S. Pat. No. 5,241,469 and issued to Nelson. The apparatus includes a printed circuit board inserted in PC internal slot and connected with PC bus from one side and with a volumetric spirometer from another side. The printed circuit board includes hardware logic for analog signal pre-processing, ADC and interface for PC bus. The software to control the printed circuit board and to analyze the received data is permanently installed in the PC. The approach implemented in this apparatus has several limitations. Installation of the printed circuit board into internal PC slot requires opening the computer case and can be performed only by a person with sufficient technical skills. Part of signal processing is implemented in the printed circuit board hardware and therefore is impossible to change or upgrade without replacing the entire printed circuit board. The specialized data acquisition software which is supposed permanently reside on the computer hard drive consumes hard drive space. If the hard drive is damaged the entire apparatus becomes non-functional. In addition, the software can become non-functional if the entire software package or some of its components are accidentally erased by a person or damaged by a computer virus. These situations would have to be recognized by a professional and would require complete software re-installation. Each software installation or update requires certain percent of time effort of a skilled personnel.

A portable device to measure parameters of expiratory air flow is described in Vitalograph manual, published by Vitalograph Ltd., Maids Moreton House, Buckingham, MK18 1SW, England, Ref. No. 07038, Issue 1, 1998. The device's data processing logic is fully implemented in its hardware. The electronic circuit of this device is responsible for air flow signal registration, analysis and presentation of the measured parameters. The device also includes digital data interface to transfer analysis results to PC via a serial port. The device sends to PC the results of data processing for storage and further analysis. Specialized software should be permanently installed on PC hard drive to allow the data transmission feature. The specialized software allows data transmission from the portable device to PC but it does not allow to send data to a remote computer. To implement this feature for the described system it would be necessary to develop and install on the PC additional custom software.

In summary, based on the disclosed prior art, current systems for collecting and processing of biomedical information follow one of two conceptual models as illustrated in FIG. 1A and FIG. 1B. Each model includes both hardware and software. Hardware in the model 1 includes set of sensors Si (at least one sensor in some cases), printed circuit cards Ci (at least one card in some cases) to process and convert analog signals into a digital form, and digital data interface providing compliance with one of the standard computer data interfaces. The software is represented by an executable modules (at least one in some cases) which permanently reside in the computer and should be pre-installed before the hardware is being used.

According to the prior art 1 presented in FIG. 1A, the Hardware Unit (HU) is responsible for collecting, processing and conversion of biomedical information registered by the sensor/s. The HU transfers the obtained information to the computer for further analysis via one of pre-selected standardized data interfaces. Thus, the data processing is distributed between hardware and software and the task distribution depends on a particular implementation.

The prior art 2 presented in the FIG. 1B differs from the model 1 in that it allows transmit information from the computer to a remote data processing center via a modem. The information may then be stored in a remote computer and analyzed by a remote user.

There is a common feature in the both models which limits their functionality: the specialized software modules should be pre-installed before the hardware is being used, and the software should permanently reside in the user's computer (or in a specialized microprocessor unit). In addition, there is need in installation of supplemental custom software modules if information transfer to a remote data processing center is required. The functionality of entire system and hardware unit in particular depends on reliability and integrity of software modules which permanently reside in the computer. If the long-term storage in the computer, where the software resides, malfunctions or integrity of software components is compromised, the entire system becomes non-functional. Such situations require involvement of a skilled professional who is capable to diagnose a problem and to re-install software if necessary. The necessity of installing specialized custom software or its upgrades to reside permanently in the computing device makes such systems for processing of biomedical information more complicated, costly and more prone to malfunctioning.

SUMMARY

The present invention provides for a system for collecting biomedical information from a patient, comprising a data measurement component, which includes at least one sensing component, the sensing component providing signals representing sensed patient data to a communications port, the communications port to allow connection to a computer system through a computer system communications port. The computer system includes pre-installed software which is responsible for requesting a specialized software module, receiving the specialized software module from the remote server and allowing the specialized software module to be executed at the computer system. The remote server includes pre-installed software which is responsible for accepting request from the computer system for the specialized software module and sending the specialized software module to the computer system according to the request. A remote server includes one or more specialized software modules, which are capable of communicating with the data measurement component through the computer system communications port. The remote server, upon receiving a request from the computer system, will transmit one of the specialized software modules which are appropriate for collecting and interpreting the signals representing sensed patient data from the at least one sensing component.

The transmitted specialized software module, after it is received by the computer system, initializes and controls the operation of the data measurement components, receives the signals representing sensed patient data from the at least one sensing component through the computer system communications port, and processes the signals into biomedical information. Optionally, the transmitted specialized software module will transmit the biomedical information to the remote server, or another remote location. The specialized software module allows the computer system user to choose an address or addresses of the remote location for sending the collected biomedical information from an existing list, to update this list by adding or removing remote locations, or to disable the data transmission to a remote location at all. The specialized software module also allows the user to designate which portion of collected data should be transmitted to a certain remote location (such as row sensed data, calculated parameters, personal information, etc.).

The present invention also provides for a method of collecting biomedical information from a data measurement component. The present invention includes the steps of connecting the data measurement component to a computer system through a communication port on the computer system, to allow the data measurement component to communicate with the computer system; then using the computer system to request from a remote server a specialized software module. The specialized software module is to control the operation of the data measurement component and collect data from it. Further steps include receiving the specialized software module by the computer system via a network connection; activating and running the specialized software module by the computer system; initializing and controlling the data measurement component by means of the specialized software module; receiving and processing data from the data measurement component through the communication port on the computer system by means of the specialized software module.

The present invention provides a cost-effective multi-channel system for collecting, processing and storing biomedical information about a patient's condition. The system and method according to the present invention is simple to use, has minimum hardware and software components and allows transmitting the patient information to the remote user if deemed necessary.

The present invention sufficiently differs from the previous ones because it does not require the software for real-time biomedical information processing to be manually installed on the user's computer and to permanently reside in the long-term storage of the computer system. In one embodiment of the present invention, the specialized software is requested from a remote server when the user is going to obtain data from sensors and is sent to the user's computer in the form of an Internet applet which controls hardware and processes information.

The present invention has several advantages over existing models. The system is cost-effective because (1) the amount of hardware components, which usually carry most of the production cost, is reduced to a minimum, and (2) there is no need in specialized software installation in the user's computer. The hardware is minimized because all functionality, which may possibly be implemented in software, is delegated to the applets allowing to strip down the hardware only to a minimal set of components (for example, sensors, ADC, data interface). The elimination of the necessity to pre-install software and to keep the software permanently on the computer saves storage space on hard drive, saves time and monetary resources necessary for professional installation, upgrade and software troubleshooting. Because the applet is sent from a remote server and is not required to be permanently stored in the user's computer the upgrade may occur seamlessly without any user involvement. Because almost all functionality is implemented in applets, and not in hardware, almost all aspects of data processing are now subject for a seamless upgrade.

Further, while adding new functionality (remote connectivity) the present invention provides much simpler operational environment because (1) the present invention does not require user involvement in software installation and upgrade, and (2) because the specialized software operates in a well known and commonly used user-friendly environment (such as Web-browser).

Still another advantage is the ease of use of the system by patients. The patient or user does not need to worry about collecting, processing and sending the data to the proper parties. This is all performed automatically, and therefore the risk of lost or incorrect data is greatly reduced. Another innovative component of this invention is that, while web browsers generally are being used to obtain patient information from users by manual data entry (using keyboard or mouse), this invention provides means to use web browser for collecting biomedical information directly from multiple bio-sensors. This allows the collection and processing of complex biomedical information with minimal patient effort and using familiar and user-friendly web-browser interface. The user therefore has a great incentive to perform such measurements since the user's effort is minimal. Therefore the present invention will help increase the usage of home biomedical sensors by patients and thereby help the patients provide themselves with the proper care.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION

Figure 1A:
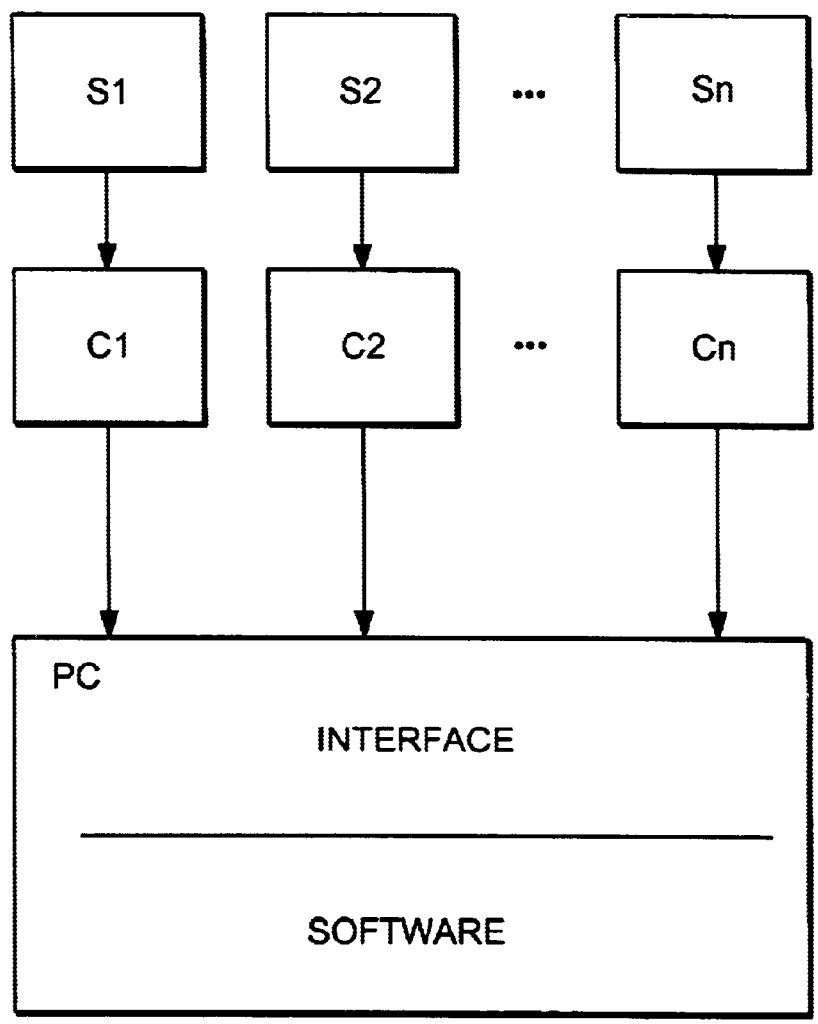
FIG. 1a shows a prior art system.
Figure 1B:
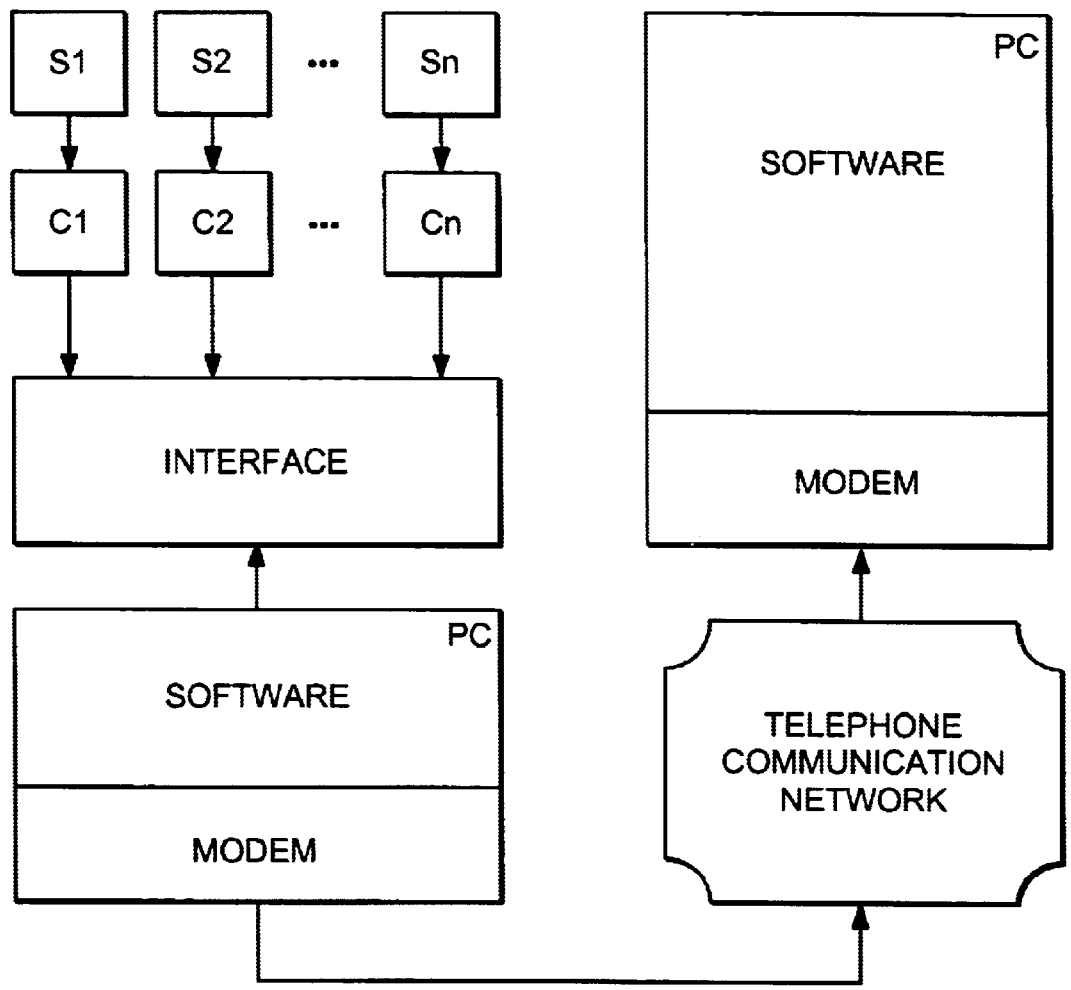
FIG. 1b shows another prior art system.
Figure 2:
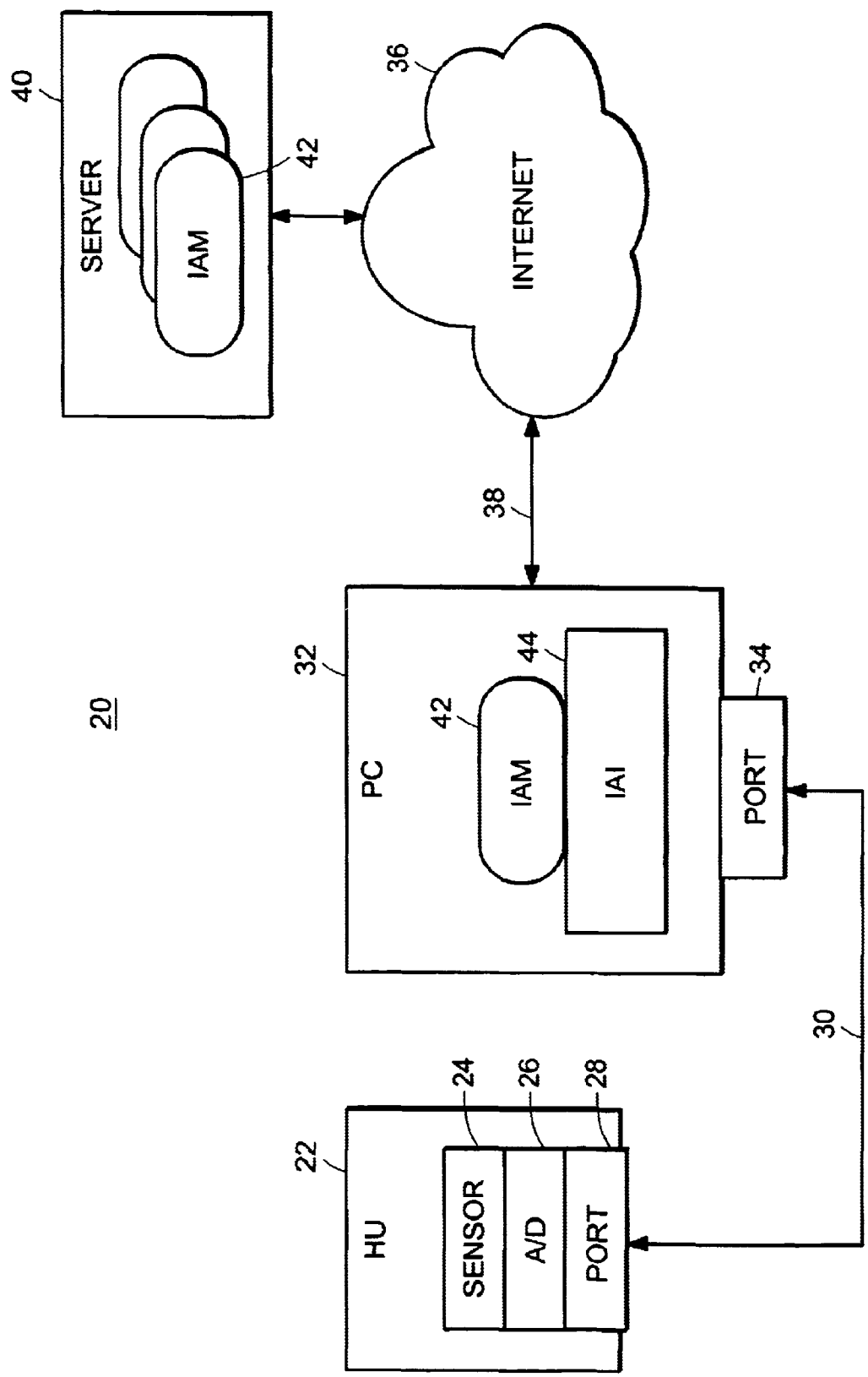
FIG. 2 is a block diagram of a system according to the present invention.
Figure 3:
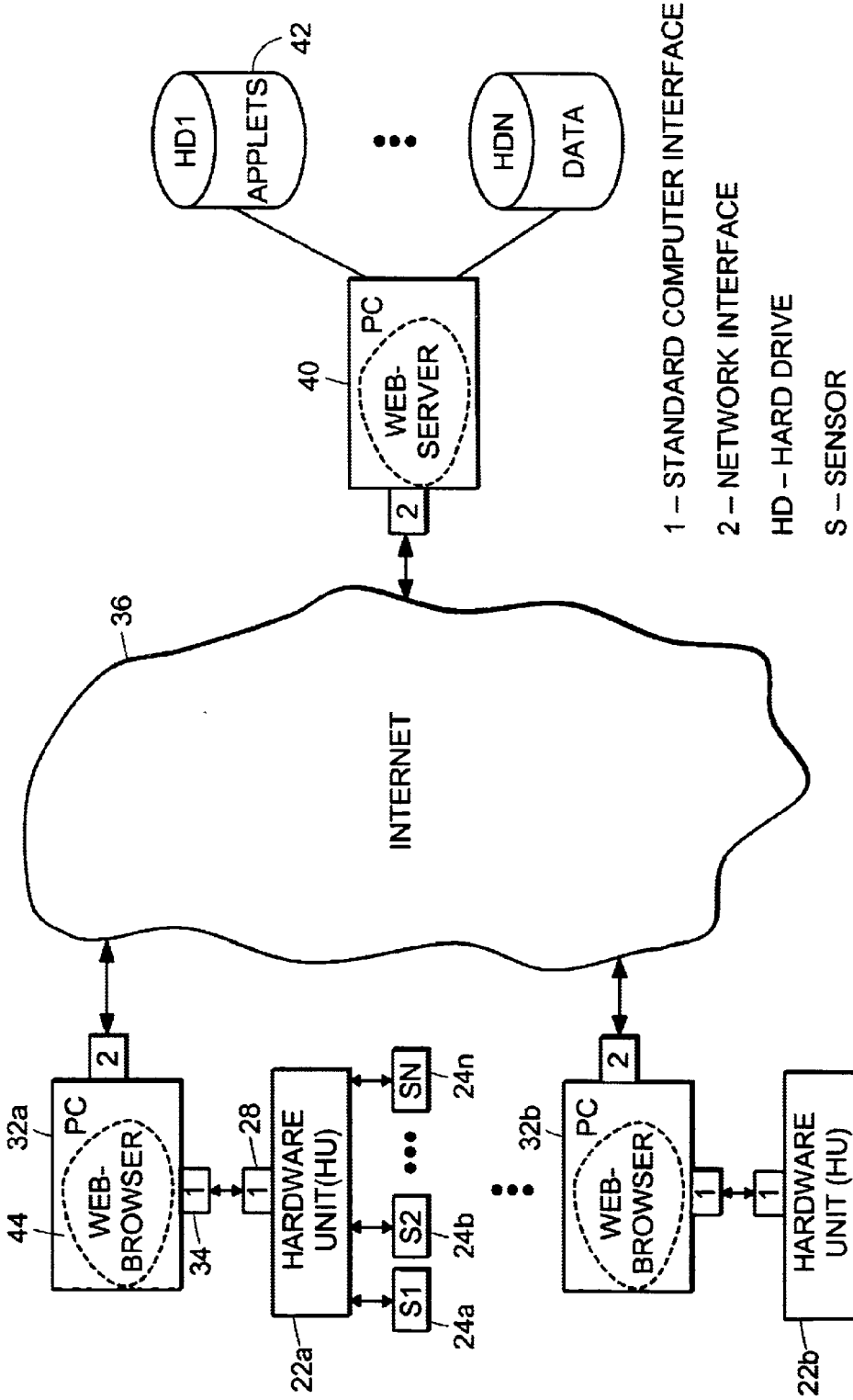
FIG. 3 is a block diagram of an illustrative embodiment of the present invention.

A system 20 according to the present invention is shown in FIG. 3. A data measurement component, or data collecting hardware unit (HU) 22 is used to perform the monitoring and data collection function. Typically the HU 22 will include a sensing component or sensor 24 which measure the data being collected. Possible sensors 24 include temperature probes, ECG, EMG, EEG, gas concentration sensors, sleep apnea sensors, air speed sensors (including flowmeters or spirometers), pressure sensors (including blood pressure monitors), chemical analysis devices, blood sugar detection etc. In most cases, the sensor 24 will measure data in an electronic analog form, for example by voltage variation, current variation, resistance or impedance changes etc. Such analog data is then converted to digital data by an A/D converter 26, as is well known in the art. If the data from sensor 24 is already in a digital form, such as pulsed signals or other digital data, then the A/D converter 26 is not necessary. Further, although a single sensor 24 is shown, multiple sensors sending providing signals to the A/D converter 26 are possible, as will be discussed below.

The data from the A/D converter 26 is then provided to a port 28 which allows transmission of the data over a line 30. The port 28 includes any circuitry necessary to prepare the data for transmission. Examples of such data transmission include PCMCIA, ISA, PCI, RS-232, USB, FIREWIRE, Bluetooth, parallel printer port configurations etc.

Although the HU 22 is shown with just a sensor 24, A/D converter 26, and port 28, other circuitry and hardware can be included, and is within the scope of the present invention. Example of other such circuitry include power sources such as internal or external batteries or power connection, internal volatile or non-volatile memory such as RAM, ROM or EEPROM, circuit controls such as a microprocessor or microcontroller; indicators to users such as LEDs, LCDs, displays, noise producers etc.

The line 30 connects the HU 22 to the port 34 on a computer system 32. Although a physical connection is shown, the ports 28, 34 may also communicate in other fashions such as infrared, radio signals etc. Typically the computer 32 is a personal computer with an RS-232 port used as the port 34. However the computer 32 can be any type of computing device such as a personal digital assistant, internet appliance etc. The computer 32 only needs to be able to connect to a communications network 36 such as the Internet, and have some type of data exchange port 34 to interface with the HU 22.

The present invention allows for a whole array of different HU 22 devices to be connected to a computer 32 and thereby measure data as required. In order to function properly, the proper measurement software must be present on the computer 32. The proper software for the HU 22 is referred to as an Intelligent Agent Module (IAM) 42. The IAM 42 typically is a specialized software module specific to the type of the HU 22, however it is within the scope of the present invention that one IAM 42 may be able to control and collect data from a variety of HU 22 devices.

In order for the proper IAM 42 to be selected, the present invention provides for the contemporaneous acquisition of the IAM 42 from a remote server 40. The remote server 40 typically includes software (such as web server software) which accepts requests for an appropriate IAM 42 and sends the proper IAM 42 back to the computer 32. When data is to be collected by the HU 22, the proper IAM 42 for the particular HU 22 is requested from the server 40, and received by the computer 32. Typically this is performed by requesting the IAM 42 and receiving it by the computer 32 from the server 40 in real time. The server 40 selects the proper IAM 42 based on many possible criteria, including the type of HU 22, information about the user, information about other parties to receive the data, etc. Once the IAM 42 is received by the computer 32, it is initialized and executed using pre-installed software. The computer 32 typically has pre-installed software or programs to request IAM 42 and assist the IAM 42 in running, such as an Intelligent Agent Interpreter (IAI) 44. The IAI 44 performs the task of requesting the IAM 42 from the remote server 40, receiving the IAM 42 by the computer 32, activating and running the IAM 42 on the computer 32. The IAI 44 may be part of computer's operating system or distributed separately. The IAI 44 (such as a web browser) may generally be implemented not only in a standard computing device (such as PC, laptop, notebook, palmtop, PDA, handheld organizers, etc.) but also in cell phones, Web TV, network PC or any other computing device capable to receive, interpret and execute IAI software components. The IAI 44 software components may reside not only in long-term storage such as a hard drive but also these components may be permanently built-in ROM or downloaded from a network (such as LAN or WAN) directly to the computer's RAM or saved in long-term storage for further use. The server 40 may help control the IAM 42 remotely.

The IAM 42 then communicates with the port 34 to obtain data from the HU 22. If necessary, the IAM 42 also sends control instructions to the HU 22. The IAM 42 receives the data from the HU 22, and then performs appropriate processing to the data. Such processing can vary from simply collecting and storing data points, to analysis and processing to convert the data into the proper information format. The data or information may be stored on the computer 32, displayed to the user on a monitor (not shown), and uploaded to the server 40.

Figure 4:
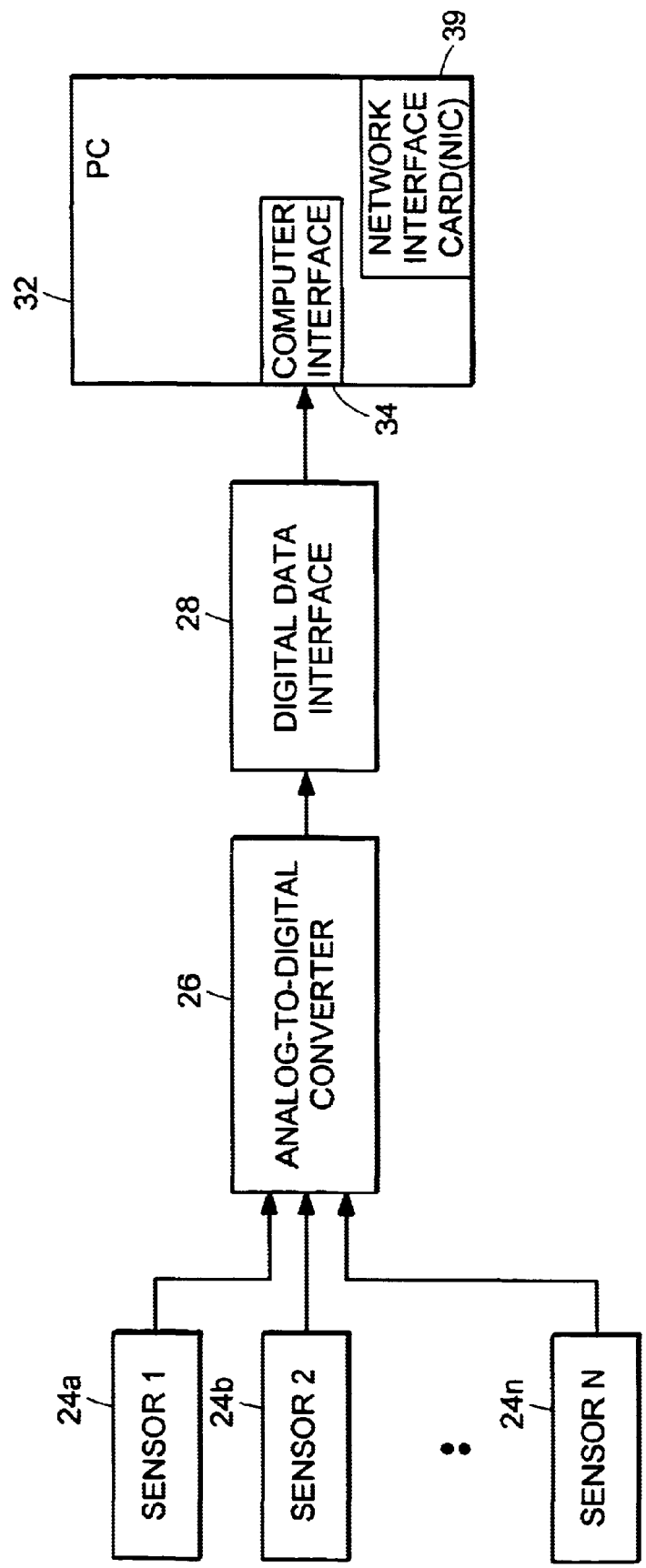
FIG. 4 is a block diagram of a hardware unit (HU) and interface of an illustrative embodiment of the present invention.

An illustrative embodiment of the present invention will now be disclosed with reference to FIG. 3 and FIG. 4. The illustrative embodiment describes collecting biomedical data from hardware unit (HU) 22 designed to measure such biomedical data. The illustrative embodiment describes a hardware unit (HU) 22 which is fully operated via Internet and comprises of a set of sensing components 24 switched (multiplexed) by means of software to the input of a single A/D serial converter 26 (see FIG. 4). The A/D converter output is connected to the converter 28 of incoming digital serial data to RS-232 interface format (or any other standard digital data format); the output of this converter is connected to the RS-232 PC serial port (or any other standard digital data format) and the control of the hardware unit, collection and processing of biomedical information is provided through the Internet 36. The Internet 36 makes possible to avoid the installation of the necessary software. The Web-browser program is installed on the user's computer in the usual manner, typically being pre-installed by the computer vendor together with the computer's operating system.

As previously noted, the illustrative embodiment simplifies software and hardware utilization and reduces cost for the multiple biomedical sensors because they are switched by means of software onto the single A/D converter and the obtained information is transferred through the RS-232 serial PC port (or any other standard digital data interface) to the user's computer for processing and analyzing.

Figure 5:
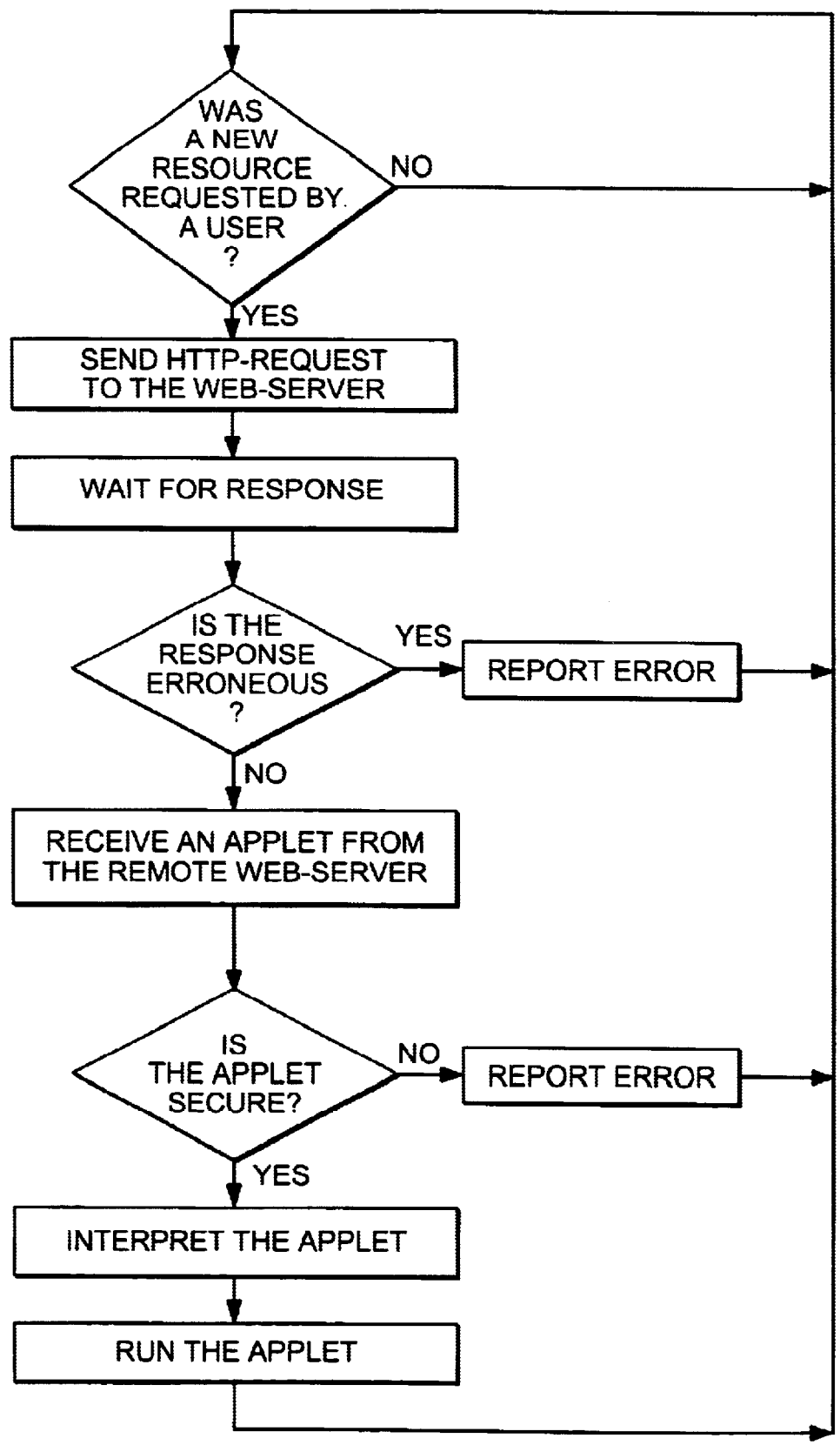
FIG. 5 is a flowchart of steps performed by a web browser according to the illustrative embodiment.
Figure 6:
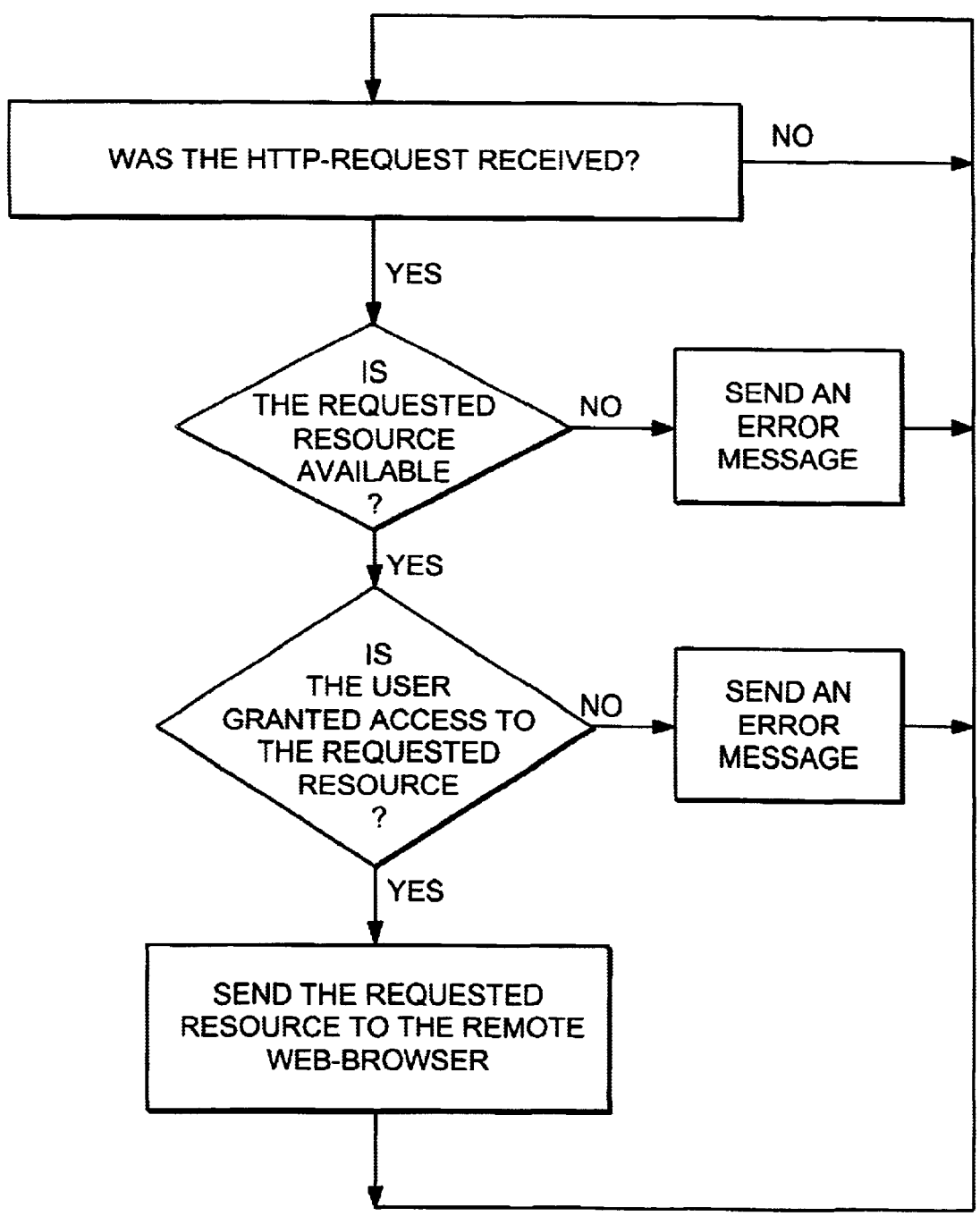
FIG. 6 is a flowchart of steps performed by a web server according to the illustrative embodiment.

In the illustrative embodiment, the Intelligent Agent Module (IAM) 42 may be implemented in various ways, including Java from Sun Microsystems and ActiveX from Microsoft Corporation. The IAM 42 is implemented as an applet. Applets in this application are considered as intelligent agents which carry out certain functionality and can be requested, accepted and operated by a local computer 32 over Internet from a remote server (usually using a Web-browser). The applets are located in the remote web server 40. The remote web server typically is a computer which includes web server software (such as Microsoft Internet Information Server, NCSA HTTP Server or CERN Web Server) which constantly listens for incoming requests for certain resources, identifies these resources and sends them back to the computer which initially requested them. The web server 40 provides the possibility to transmit applets to any web browser 44, located in the user's computer that supports HTTP or XMP protocol. The IAI 44 is presented by software installed on a local PC which allows requesting the IAM 42 from a remote web server 40, to receive the IAM 42 at the local PC, and to interpret and execute the received IAM 42 on the local PC. The IAI 44 typically is implemented as a standard software routinely installed by PC vendor as a web browser (such as Microsoft Internet Explorer or Netscape Navigator). Typically a user starts data collection by choosing a highlighted text message in the web browser window. When a user clicks on the corresponding hypertext (URL) link which uniquely identifies the location of the IAM 42 at the remote server, the web browser 44 sends a request to the web server 40, which in turn sends the requested applet to the web browser 44. In response the web browser 44 activates and starts the received applet. Steps performed by the web browser 44 are illustrated in FIG. 5, and steps performed by the web server 40 are illustrated in FIG. 6.

For receiving or downloading the applet to the computer 32 and/or for receiving information based on the data collection, the web server 40 and web browser 44 may set up a secure connection, as is known in the art. This secure connection allows for a high level of data security through the use of data encryption and certificates, thereby protecting the privacy of the user, along with the information obtained during the data collection.

Figure 7:
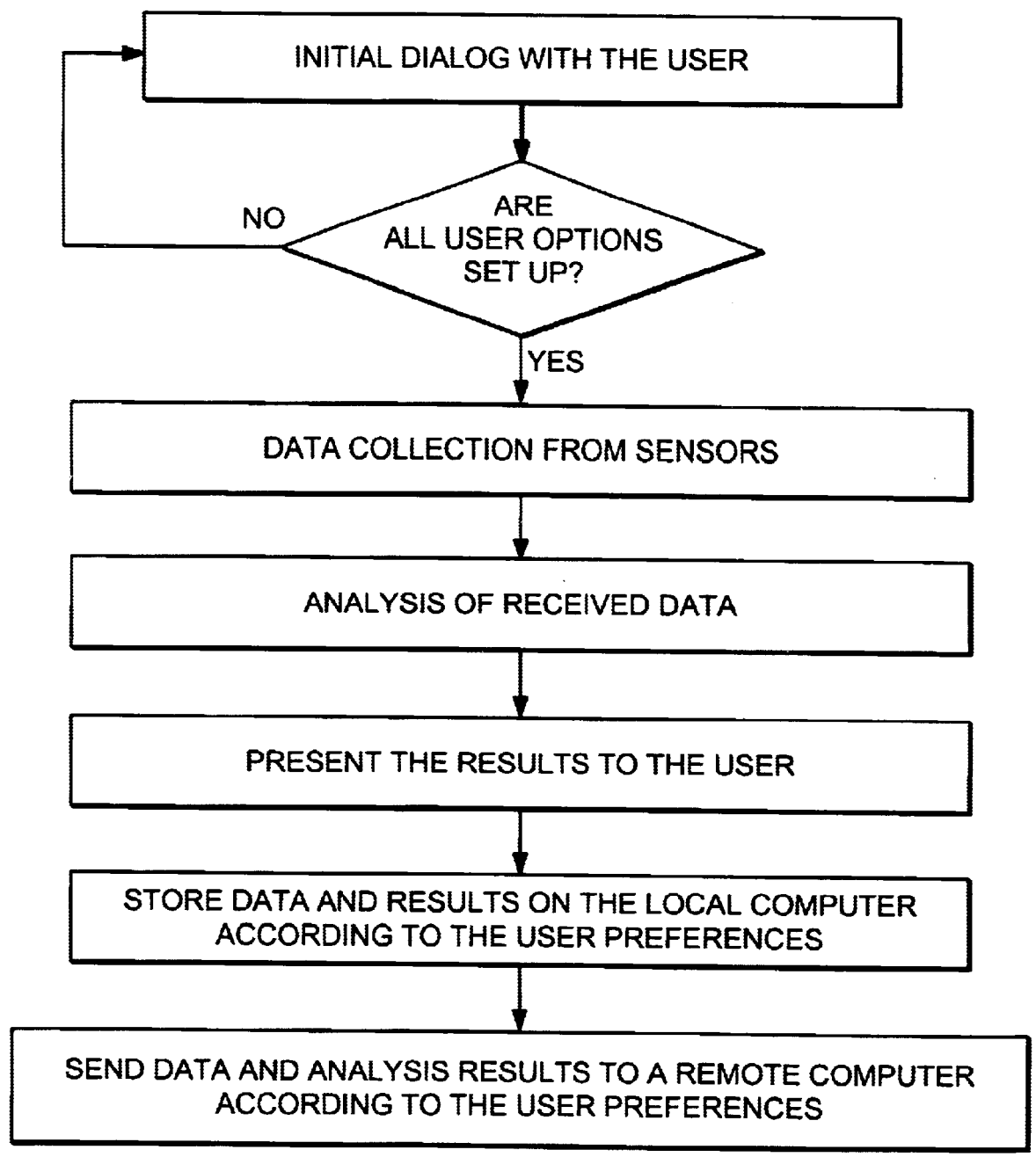
FIG. 7 is a flowchart of steps performed by a received program according to the illustrative embodiment.

Once the applet is loaded onto the computer 32 and activated, it can perform the data collecting activities. Steps performed by an applet according to the illustrative embodiment are given in FIG. 7. If data needs to be collected from the user, the applet can perform an initial dialog using the web browser interface to present fields or dialog boxes to allow for user data entry. These fields or dialog boxes may also contain pre-filled in data as obtained by the server, in order to assist the user in only requiring the user to change and enter data if the pre-filled in data is incorrect or out of date. The applet can also display instructions to the user on the proper steps to be taken in order to collect data, along with selectable help features for any areas where the user has questions.

The applet or specialized software module may comprise a varying set of software components, including a proper set of software components for receiving data from the set of sensing components 24 in the hardware unit 22, and a set of software components for processing the data in the proper form based on patient requirements, medical data requirements, and also requirements for the remote location the biomedical information will be transmitted to. For example, a remote location would require data in a certain format (such as CORBA or the interface definition language (IDL)). Therefore the specialized software module can include a number of 'mixed and matched' software components based on the unique requirements of the patient. Further the received specialized software module may request other software modules be sent by the remote server, thereby allowing discrete software components to be received in succession, or only as needed. For example the specialized software module may receive and collect data from the hardware unit 22, then request and receive software components to process the data in a form as required by the patient, and then request and receive software components to display the data to the patient, and to transmit the data to a remote location.

Figure 8:
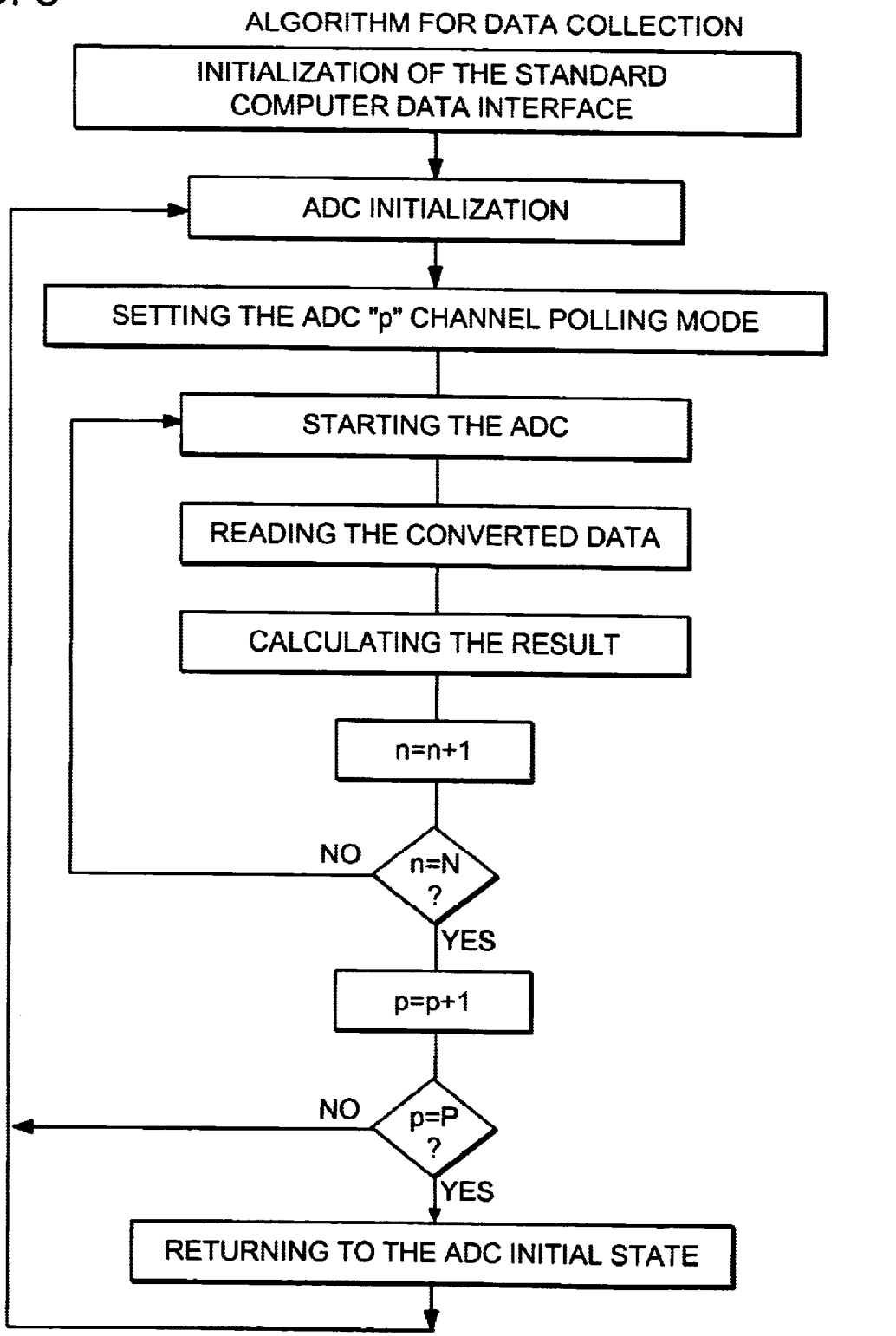
FIG. 8 is a flowchart of steps performed by during data collection according to the illustrative embodiment.

Steps performed by the illustrative embodiment during data collection are illustrated in FIG. 8. In the case of multiple sensors providing data simultaneously, the data is multiplexed, and the proper data points are polled in order to get data from the individual sensors.

Figure 9:
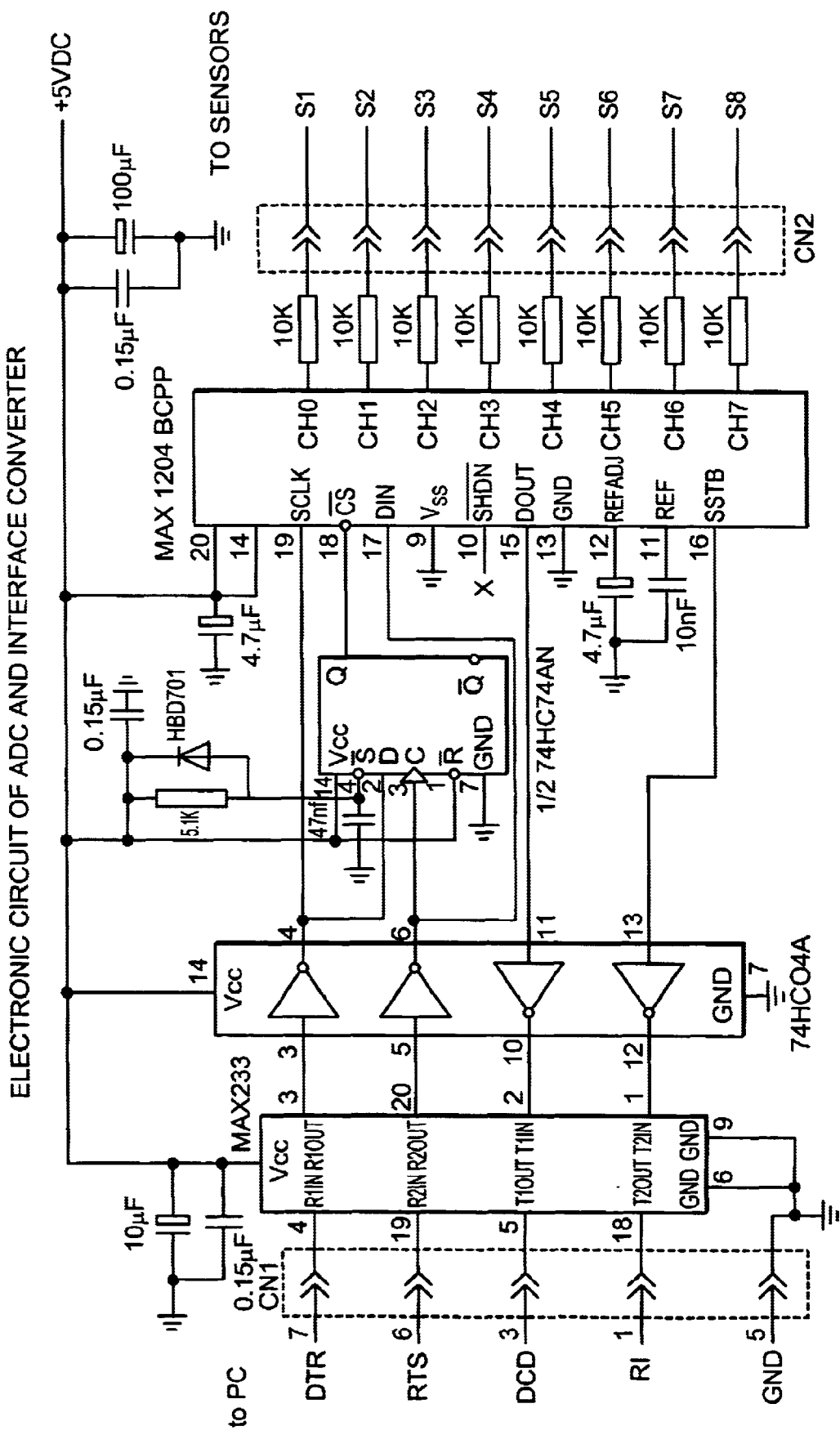
FIG. 9 is a circuit diagram of another embodiment of a hardware unit according to the present invention.

FIG. 9 shows a schematic of a hardware unit (HU) 22 for the illustrative embodiment. It includes a serial 8-channel A/D converter with software switching inputs and a signal converter to RS-232 interface format. This HU 22 can accept input from up to 8 sensors and provide the data to a computer through the RS-232 serial port.

Figure 10A:
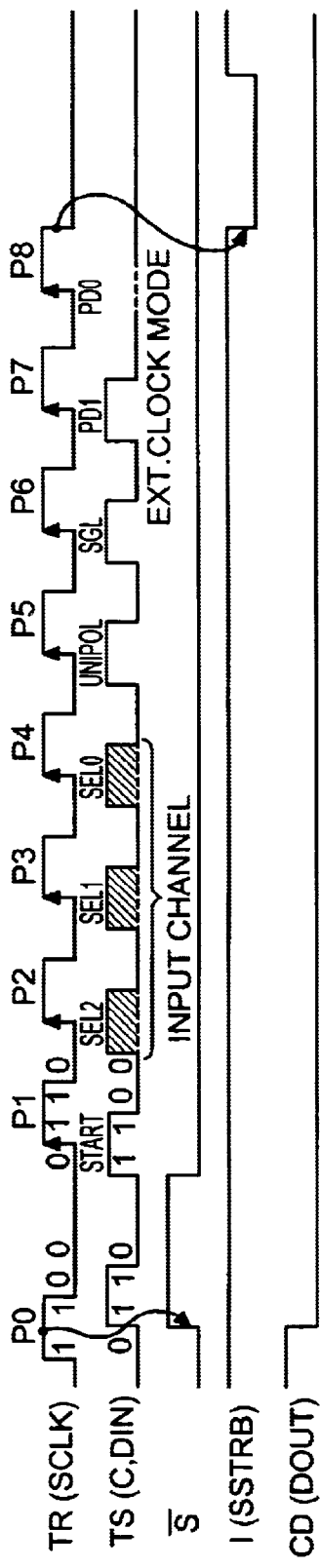
FIG. 10 is a timing signal chart for the hardware unit of FIG. 9.
Figure 10B:
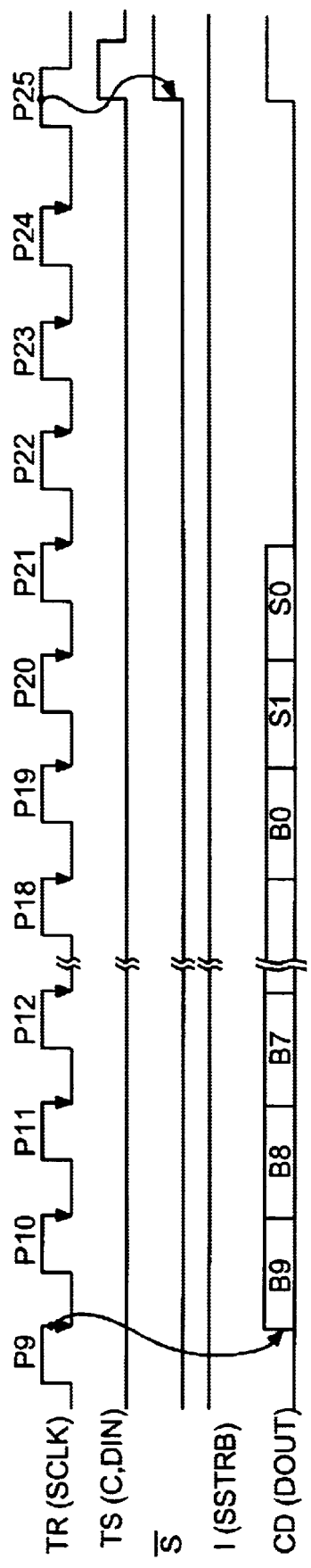

The time diagram of the circuitry signals for the circuit in FIG. 9 is shown in FIG. 10. According to the time diagram at first through the modem control register (DTR and RTS signals) to the A/D converter the configuration word is written and thus one of 8 analog input channels is selected (see pulses START . . . PD0 in FIG. 10.1). The A/D configuration bits are written into the A/D by the rising edge of the pulse synchronizing sequence P1 . . . P8 (DTR signal, FIG. 10.1). The first starting pulse is equal to 1, and 4 last configuration pulses, corresponding to P5 . . . P8 pulses of the synchronizing sequence determines the following A/D operation regime: the unipolar mode of operation (0V . . . 4.096V), non-differential input (SGL), internal clocking (PD1=1, PD0=0).

The trailing edge of the P8 pulse forces the A/D to start the conversion and simultaneously the signal SSTRB changes to 0 for the time of conversion (approx. 10 μsec). After the end of conversion the 10-bit data is serially clocked out by the trailing edge of the DTR signal (see FIG. 10.2).

To write information into the computer, the modem control register of the RS-232 serial port is used (DCD and RI signals of the serial port). After the P8 pulse PC is waiting the low level of SSTRB signal, and after it is achieved, the computer is waiting the condition when this signal is set to 1 which means the end of conversion cycle.

The PC produces clock-out pulses P9 . . . P21 and after each such pulse the corresponding bit of 10-bit result word is read from the DCD serial interface output. The following three pulses P22–P24 clock-out terminated zeroes.

To control the CS signal the phase attitude of DTR and RTS signals are used. To set the CS signal the rising edge of the pulse on the RTS input is delayed respectively to P25 (see FIG. 10.2), and the reset of CS is performed by the rising edge of the START pulse on the RTS input (see FIG. 10.1, pulse P1). It can be seen from FIG. 10.1 that to form on the DTR and RTS inputs the required relative pulse position it is necessary to provide four write operations into modem control register for each pulse to be formed.

Figure 11:
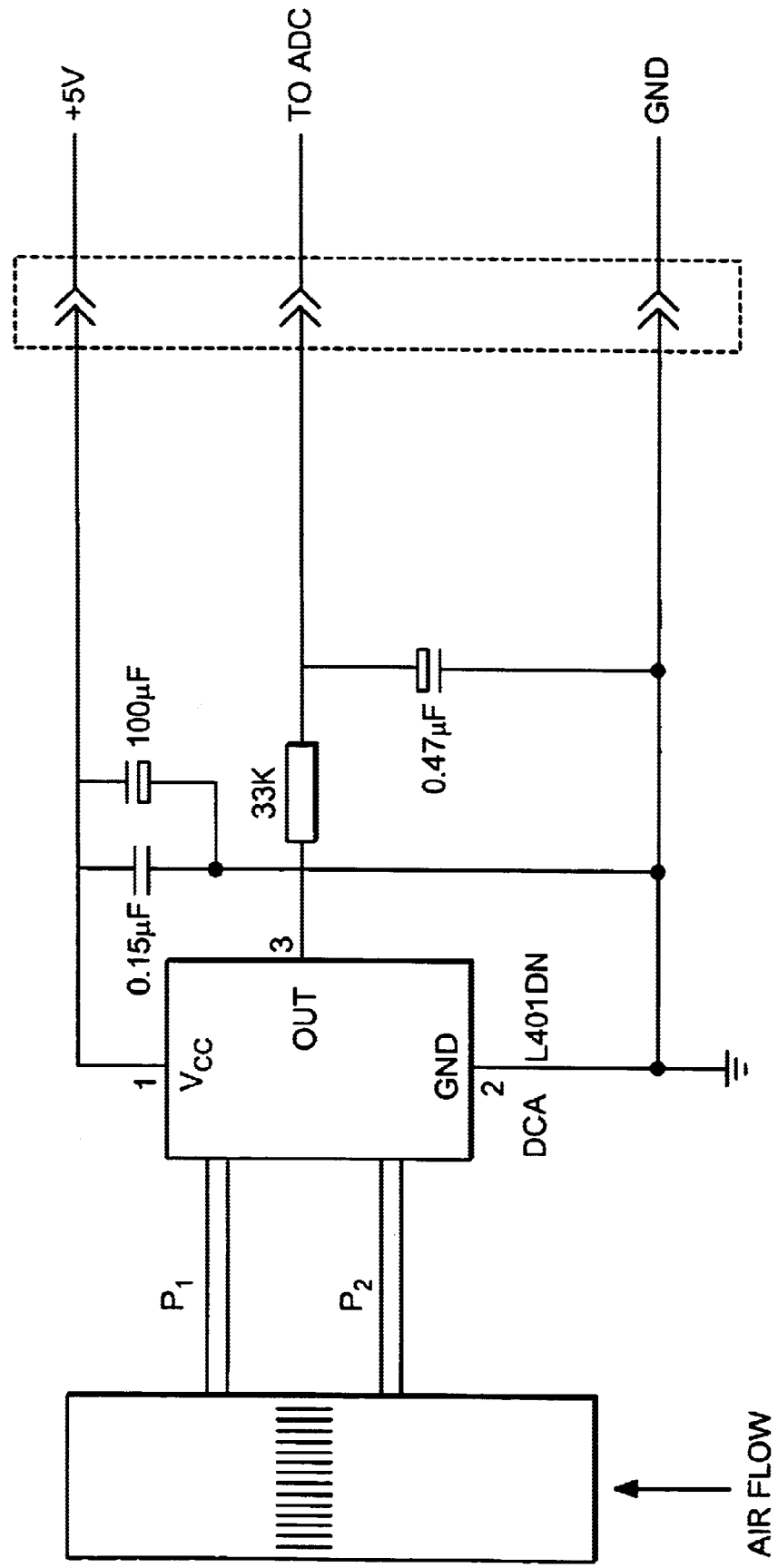
FIG. 11 is a circuit diagram for a flow sensor for use with the hardware unit of FIG. 8.
Figure 12:
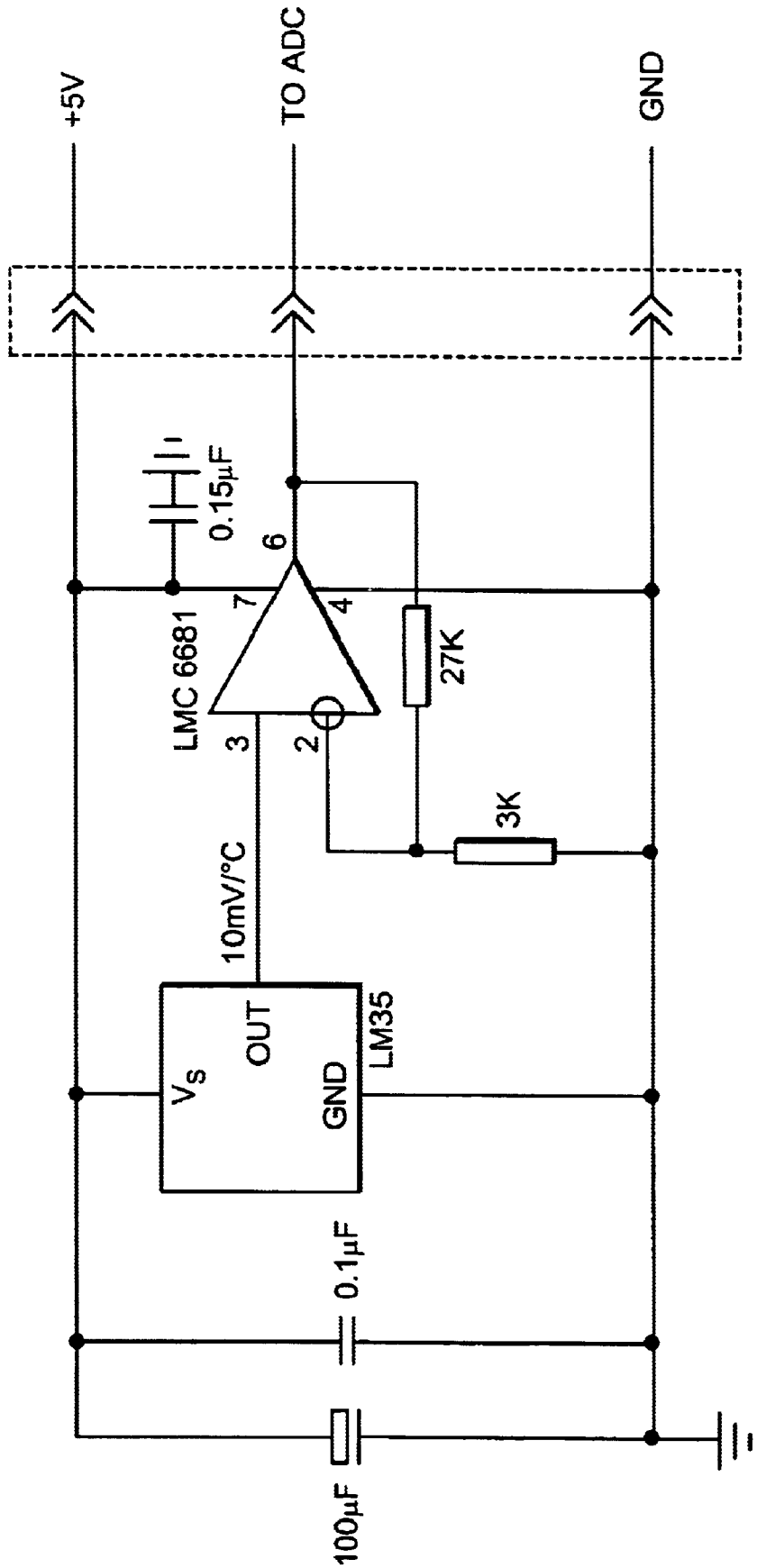
FIG. 12 is a circuit diagram for a temperature sensor for use with the hardware unit of FIG. 8.

An embodiment of the present invention for use as a portable flowmeter is illustrated in FIG. 11 and FIG. 12, which utilizes Microsoft Internet Explorer web browser software. The portable flowmeter measured the parameters of expiratory flow and ambient temperature. For this purpose expiratory flow velocity electronic measurement circuitry, FIG. 11, and temperature sensing measurement circuit, FIG. 12 was designed. The flow velocity sensor, FIG. 11, includes a tube with incorporated into it a flow resistive element. At the entrance and exit of the flow resistive element small holes in the tube to measure a pressure drop (P1–P2) are formed. The difference of these pressures is proportional to the measured flow velocity. This difference is transformed by means of Data Instruments DCAL401DN Integrated Circuit to the electrical signal. This signal through a RC-filter circuit is applied to one of the A/D converter's inputs. The temperature sensor electronic circuit, FIG. 12 is based on the National Semiconductor's LM35 Integrated Circuit. For signal scaling the LMC6681 Integrated Circuit is used the output of which is connected to one of the A/D inputs.

Although the invention has been shown and described with respect to illustrative embodiments thereof, various other changes, omissions and additions in the form and detail thereof may be made therein without departing from the spirit and scope of the invention.

What is claimed is:

1. A method of collecting biomedical information from a data measurement component, comprising:
   connecting said data measurement component to a computer system through a connection on said computer system to allow said data measurement component to communicate with said computer system;
   using said computer system to request from a remote server a specialized software module for collecting and processing biomedical information;
   receiving said specialize software module by said computer system sent from the remote server;
   activating and running said specialized software module by said computer systems wherein said specialized software initializes and controls said data measurement component; and
   receiving and processing data from said data measurement component through said connection on said computer system by said specialized software module.

2. The method of claim 1 further including the step of said specialized software module sending said received and processed data to a remote location.

3. The method of claim 1 wherein said connection on said computer system includes a data communications port.

4. The method of claim 3 wherein said data communications port communicates using a protocol elected from the group of PCMCIA, ISA, PCI, RS-232, and USB.

5. The method of claim 1 wherein said data measurement component includes a plurality of sensing components, said sensing components to sense different biomedical data.

6. The method of claim 5 wherein said plurality of sensing components send signals to an analog-to-digital component, said analog-to-digital component to process and encode said signals from said plurality of sensing components and to send said encoded data to said computer system.

7. The method of claim 1 wherein said specialized software module includes plurality of software components, said software components to collect and process biomedical data.

8. The method of claim 1 wherein said computer system includes pre-installed software which is responsible for requesting said specialized software module, receiving said specialized software module from said remote server and allowing said specialized software module to be executed at said computer system.

9. The method of claim 8 wherein said pre-installed software includes a web-browser.

10. The method of claim 1 wherein said remote server includes pre-installed software which is responsible for accepting a request from said computer system for said specialized so are module and sending the said specialized software module to said computer system according to said request.

11. The method of claim 10 wherein said remote server includes a web-server.

12. A system for collecting biomedical information from a patient comprising:

a data measurement component including at least one sensing component, said at least one sensing component pr viding signals representing sensed patient data to a communications port, said communications port to allow connection to a computer system through a computer system communications port;

a remote server including a plurality of specialized software modules, each specialized software module uniquely configured for collecting said signals representing sensed patient data from a particular at least one sensing component, and wherein each of said specialized software modules includes means for communicating with said data measurement component through said computer system communications port, wherein said remote server, upon receiving a request from said computer system, will transmit at least one of said specialized software modules based on said at least one sensing component;

wherein when said transmitted specialized software module is received by said computer system; said transmitted specialized software module initializes and controls said data measurement component, receives said signals representing sensed patient data from said at least one sensing component through said computer system communications port, and processes said signals into biomedical information.

13. The system of claim 12 wherein said transmitted specialized software module, upon processing said signals into biomedical information, transmits said biomedical information to a remote location.

14. The system of claim 12 wherein said specialized software module is implemented as an Internet applet.

15. The system of claim 12 wherein said data measurement component includes an analog-to-digital component to process said signals representing sensed patient data from said at least one sensing component and to transmit data to said computer system by said communications port controlled by said specialized software module.

16. The system of claim 15 wherein said data measurement component includes a multichannel analog-to-digital converter to encode sensed patient data from a plurality of said sensing components.

17. The system of claim 16 wherein said specialized software module initializes communications with said data measurement component, including initialization of said analog-to-digital component, and selecting at least one data channel from said multichannel analog-to-digital converter.

18. The system of claim 12 wherein said specialized software module includes a user interface to provide information to said patient and to receive input from said patient.

19. The system of claim 12 wherein said computer system communication port communicates using a protocol selected from the group of PCMCIA, ISA, PCI, RS-232, and USB.

20. The system of claim 12 wherein said computer system includes a web browser to request, activate and run said specialized software modules.

21. The system of claim 12 wherein said remote server includes a web server to accept requests from a web browser on said computer system and to send the requested specialized software modules to said computer system.

22. The system of claim 12 wherein said specialized software module, upon being received by said compute system, requests said remote server to transmit other software modules to said computer system, said other software modules to assist in processing biomedical information.

23. A system for collecting biomedical information from a patient comprising:

a data measurement component including sensing means for sensing patient data and sending said patient data to a computer system;

a remote server including a plurality of specialized software modules, wherein each of said specialized software modules includes communication means for receiving patient data from said data measurement component, wherein said remote server, upon receiving a request from said computer system, will transmit one of said specialized software modules, said transmitted specialized software module including means for processing said sensed patient data from said data measurement component into biomedical information;

wherein when said transmitted specialized software module is received by said computer system; said transmitted specialized software module initializes and controls said data measurement component and receives said patient data from said data measurement component.

24. The system of claim 23 wherein said transmitted specialized software module includes mean for sending said biomedical information to said remote server.

* * * * *